United States Patent [19]

Sandermann et al.

[11] 4,085,220

[45] Apr. 18, 1978

[54] 2-ALKENYL-N-[(TRICHLOROMETHYL)THIO]SUCCINIMIDES

[75] Inventors: Wilhelm Sandermann, Donaustauf; Heinz Eggensperger, Hamburg; Karl-Heinz Diehl, Norderstedt, all of Germany

[73] Assignee: Sterling Drug Inc., New York, N.Y.

[21] Appl. No.: 782,750

[22] Filed: Mar. 30, 1977

[30] Foreign Application Priority Data

Apr. 7, 1976 Germany .................... 2614935

[51] Int. Cl.$^2$ .................... C07D 207/40; A61K 31/40
[52] U.S. Cl. ........................... 424/274; 260/326.5 S
[58] Field of Search ................ 260/326.5 S; 424/274

[56] References Cited

U.S. PATENT DOCUMENTS

| 2,553,770 | 5/1951 | Kittleson | 260/326.55 |
| 2,553,771 | 5/1951 | Kittleson et al. | 260/326.5 S |

OTHER PUBLICATIONS

Allen R. Kittleson, J. Agr. Food Chem. 1, 677–679, (1953).

Primary Examiner—Jose Tovar
Attorney, Agent, or Firm—Frederik W. Stonner; B. Woodrow Wyatt

[57] ABSTRACT

The invention relates to 2-R-N-[(trichloromethyl)thio]succinimides, where R is alkenyl having from 8 to 12 carbon atoms, useful as fungicidal agents, to fungicidal compositions containing them, and to methods for their use.

9 Claims, No Drawings

2-ALKENYL-N-[(TRICHLOROMETHYL)THIO]-SUCCINIMIDES

BACKGROUND OF THE INVENTION

1. Field of the Invention

The invention relates to 2-R-N-[(trichloromethyl)thio]succinimides represented by the structural formula

I where R is alkenyl having from 8 to 12 carbon atoms, useful as fungicidal agents, to compositions containing them, and to methods for their use.

2. Description of the Prior Art

Fungicides find application as plant protectants, for the preservation of wood, leather, lacquer, textiles, paper and other organic materials, and in combating fungus infections in animals and man. Many of these fungicides, however, have certain disadvantages. Thus, organic mercury compounds are toxic, organic tin compounds are light sensitive, chlorophenols like pentachlorophenol are volatile and toxic to man, while derivatives of dithiocarbamic acids react with metal siccatives to darken lacquers.

The trichloromethylthio compounds described in U.S. Pat. No. 2,553,770 are good, long acting fungicides whose action is due to the blocking of SH-groups in phosphorylating enzymes, cf. R. G. Owens and H. M. Novotny, Contr. Boyce Thompson Inst., vol. 20, p. 171 (1959). These fungicides are prepared by the reaction of the appropriate dicarboxylic acid imide with trichloromethanesulfenyl chloride. The imides employed as starting materials in this reaction are endomethylenetetrahydrophthalimide, phthalimide, tetrahydrophthalimide and succinimide. Of the compounds prepared in this manner, primarily compounds represented by the formulas II to IV below are encountered as items of trade.

II Captan

III Phaltan (Folpet)

IV

In addition, fluorinated compounds having formulas V and VI below have been developed:

V Fluorfolpet (Preventol A3)

VI Dichlo fluamid

The properties of the foregoing identified trichloromethylthio compounds in practical use have been reported in "Fette, Seifen, Anstrichmittel", vol. 68, (1966) pp. 275–279 and B. A. Richardson, B.W.P.A. Annual Convention (1972), chapter (6), sapstain control, p. 9. The fungicidal effect of these known agents towards wood- and paint-damaging fungi depends largely on their solubility in petroleum hydrocarbons. Thus, Captan, a good acting fungicide for plant protection, is ineffective against wood- and paint-damaging fungi, owing to its low solubility in petroleum solvents, see B. A. Richardson, loc. cit. The compound IV, obtained from hexahydrophthalimide, is only 0.3% soluble in mineral spirits. Such a low solubility is for most purposes insufficient.

Recently, an important factor in evaluating fungicides has been their harmlessness to man. Certain trichloromethylthio compounds, such as Capstan (II) and Folpet (III), recently have become suspect as producing malformation-causing mutations, cf. "Umschau" 1970 p. 652 and P. Schulster in "Die Zeit" of date 4 January 1974. Apparently the phthalimide structure of these fungicides is responsible for the detrimental effects. Of interest in this connection is the fact that the malformation-causing Contergan (thalidomide) (VII) also has the same phthalimide structure.

VII

In developing new fungicides therefore, certain properties are desirable. Thus, a good fungicide should:

(1) have good activity of long duration,
(2) be very soluble in petroleum hydrocarbons; and
(3) be harmless in use.

Since fungicides of the type of N-trichloromethylthiodicarboxylic acid imides have long duration of action, extensive investigations were carried out with an aim to finding fungicides of that type which fulfill these requirements. It was found that of a large number of synthetically prepared compounds, by no means all compounds of general structural formula display fungicidal activity as disclosed in U.S. Pat. No. 2,553,770 notes hereinabove. Rather, activity is associated with strictly defined structural features. Thus, the trichloromethylthio compounds obtained from anthracene-maleic anhydride adduct, caryophyllen-maleic anhydride adduct, isoeugenol-maleic anhydride adduct, homophthalic anhydride, camphoric anhydride, hexadecyl succinic anhydride and many other anhydrides are inactive.

SUMMARY OF THE INVENTION

After considerable experimentation resulting in compounds having poor or no fungicidal activity and poor solubility, and physiologically questionable compounds, a class of compounds was discovered which unexpectedly possesses favorable properties.

Thus in the compound aspect of the invention there is provided a 2-R-N-[(trichloromethyl)thio]succinimide represented by the structural formula I hereinabove where R is alkenyl having from 8 to 12 carbon atoms.

The compounds of the invention represented by structural formula I have fungicidal activity of long duration and are readily soluble in petroleum hydrocarbons.

In the composition aspect of the invention there is provided a fungicidal composition comprising as active fungicidal ingredient at least one 2-R-N-[(trichloromethyl)thio]succinimide represented by the structural formula I hereinabove, where R is alkenyl having from 8 to 12 carbon atoms, and a carrier therefor.

In a method aspect of the invention there is provided a method for preventing or retarding the deleterious effects associated with fungus contamination on a material susceptible to fungus contamination which comprises treating the material with a fungicidally effective amount of at least one 2-R-N-[(trichloromethyl)thio]-succinimide represented by the structural formula I hereinabove, where R is alkenyl having from 8 to 12 carbon atoms.

Throughout the specification, it will be understood that alkenyl, as represented by R in formula I, can be straight or branched and that the double bond thereof may occur at any available position.

DETAILED DESCRIPTION INCLUSIVE OF THE PREFERRED EMBODIMENTS

The compounds of structural formula I are prepared using generally known procedures. Thus an anhydride represented by the general structural formula

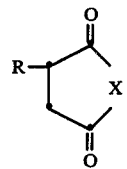

VIII where X represents oxygen (O) and R has the same meaning disclosed hereinabove for formula I, is heated with ammonium hydroxide, or is heated under pressure with saturated alcoholic ammonia solution, to give the corresponding imide of structural formula VIII (X=NH), the sodium salt of which is then treated in a suitable solvent, such as dioxane, benzene, an alcohol, or water, with trichloromethanesulfenyl chloride to give compound I.

It was surprisingly found that the compounds of the invention represented by formula I possess the desired properties defined hereinabove while corresponding compounds wherein the side chain is saturated do not exhibit these properties. Thus in comparing the alkenyl compounds of the invention with the alkyl compounds the following surprising results were noted:

(1) The alkenyl compounds of the invention are greatly superior to the alkyl compounds in fungicidal activity (cf. Table 1). Of the representative alkyl compounds, only the octyl compound is active, the decyl, dodecyl and hexadecyl compounds being inactive, while the octenyl, 2-isooctenyl, 1-decenyl and dodecenyl compounds of the invention display high fungicidal activity. The 1-hexadecenyl compound however is inactive, probably owing to its low solubility.

(2) The alkenyl compounds of the invention are markedly more soluble in mineral spirits than the alkyl compounds. Thus, the octenyl, 1-decenyl and dodecenyl compounds of the invention are respectively 25, 50 and 33 times as soluble in mineral spirits as the corresponding alkyl compounds (cf. Table 2).

(3) Finally, the solubility of the alkenyl compounds of the invention is by far greater than that of the known fungicides II, IV and VI (cf. Table 2).

In Tables 1 and 2 below, the alkenyl compounds and corresponding alkyl compounds listed can be represented by the general structural formula I hereinabove where R, for the purpose of the tables, represents either alkyl or alkenyl, although it is to be understood that the compounds of the invention are limited to those where R is alkenyl of 8 to 12 carbon atoms as hereinbefore defined.

The minimum inhibitory concentration against several microorganisms of a number of 2-alkenyl-N-[(trichloromethyl)thio]succinimides and corresponding 2-alkyl compounds as well as of Captan (II above) is presented in Table 1.

Table 1

| Compound R (formula I) | Minimum Inhibitory Concentration (%) Microorganism | | | | | | |
|---|---|---|---|---|---|---|---|
| | 1 | 2 | 3 | 4 | 5 | 6 | 7 |
| octyl | 0.05 | 0.005 | 0.005 | 0.005 | 0.005 | 0.005 | 0.005 |
| octenyl | 0.01 | 0.005 | 0.01 | 0.005 | 0.005 | 0.005 | 0.01 |
| 2-nonenyl | 0.05 | 0.005 | 0.005 | 0.005 | 0.005 | 0.005 | 0.005 |
| decyl | 0.05 | 0.1 | 1 | 1 | 0.5 | 0.5 | 1 |
| 1-decenyl | 0.01 | 0.005 | 0.1 | 0.01 | 0.05 | 0.005 | 0.1 |
| dodecyl | 0.05 | 1 | 1 | 1 | 1 | 1 | 0.1 |
| dodecenyl | 0.0005 | 0.001 | 0.1 | 0.001 | 0.001 | 0.0001 | 0.005 |
| hexadecyl | 1 | — | — | — | — | — | — |
| 1-hexadecenyl | 1 | — | — | — | — | — | — |
| Captan (II) | 0.05 | 0.01 | 0.05 | — | 0.005 | — | 0.01 |

1 *Staphylococcus aureus*
2 *Penicillium glaucum*
3 *Aspergillus niger*
4 *Sclerophoma pityophila*
5 *Pullularia pullulans*
6 *Saccharomyces cerevisiae*
7 *Candida albicans*

The percent solubility in mineral spirits at 20° C. of several 2-alkenyl-N-[(trichloromethyl)thio]succinimides and corresponding 2-alkyl compounds as well as the compounds II, IV and VI disclosed hereinbefore is presented in Table 2.

Table 2

| Compound R (formula I) | % Solubility in Mineral Spirits | Ratio of Solubilities alkenyl/alkyl |
|---|---|---|
| octyl | 0.2 | 25 : 1 |
| octenyl | 5 | |
| decyl | 0.1 | 50 : 1 |
| 1-decenyl | 5 | |
| dodecyl | 0.06 | |

Table 2-continued

| Compound R (formula I) | % Solubility in Mineral Spirits | Ratio of Solubilities alkenyl/alkyl |
|---|---|---|
| dodecenyl | 2 | 33 : 1 |
| hexadecyl | 0.025 | |
| 1-hexadecenyl | 0.2 | 4 : 1 |
| II | nearly insoluble | |
| IV | 0.3 | |
| VI | 1.2 | |

It should be noted that the compounds of the invention, in contrast to the known compounds II to V, do not contain the phthalimide moiety. In the body the unsaturated side chain of the compounds of the invention is easily oxidatively cleaved at the ethylenic double bond, and after hydrolysis of the imide bond, a succinic acid derivative is obtained. Succinic acid and its derivatives are components of the citric acid cycle in the body of man and animal. Hence, the compounds according to the invention do not represent an ecologic burden as do the known phthalimides.

The invention is illustrated by the following examples without, however, being limited thereto.

General Procedure For Preparing The Compounds Of Formula I

The 2-alkenylsuccinic anhydride (1 mole) is slowly heated with 200 ml. of ammonium hydroxide (s.g. 0.91) to 250° C. until ammonia is no longer liberated, using a condenser of a length which allows ready evaporation of water. The resulting 2-alkenylsuccinimide is dissolved in 500 ml. of 2N ethanolic sodium hydroxide, the ethanol is distilled off in vacuo, and the resulting sodium salt of the imide is suspended in 500 ml. of dioxane. To this suspension is added slowly, with gentle stirring, trichloromethanesulfenyl chloride (1.1 moles) in 200 ml. of dioxane and the reaction mixture then is heated for 30 minutes at 80° C. The mixture is allowed to stand overnight, filtered from sodium chloride, and concentrated in vacuo to give the 2-alkenyl-N-[(trichloromethyl)thio]succinimide.

Following the above-described procedure and using:

(1a) 2-octenylsuccinic anhydride;
(2a) 2-(2-isooctenyl)succinic anhydride;
(3a) 2-(2-nonenyl)succinic anhydride;
(4a) 2-(1-decenyl)succinic anhydride;
(5a) 2-undecenylsuccinic anhydride; and
(6a) 2-dodecenylsuccinic anhydride there was obained respectively:

(1b) 2-octenylsuccinimide;
(2b) 2-(2-isooctenyl)succinimide;
(3b) 2-(2-nonenyl)succinimide;
(4b) 2-(1-decenyl)succinimide;
(5b) 2-undecenylsuccinimide; and
(6b) 2-dodecenylsuccinimide which was then converted respectively to:

(1c) 2-octenyl-N-[(trichloromethyl)thio]succinimide ($n_D$ 1.5163);
(2c) 2-(2-isoocentyl)-N-[(trichloromethyl)thio]succinimide (m.p. 96° C./alcohol or benzene);
(3c) 2-(2-nonenyl)-N-[(trichloromethyl)thio]succinimide ($n_D$ 1.5135);
(4c) 2-(1-decenyl)-N-[(trichloromethyl)thio]succinimide (m.p. 56° C.);
(5c) 2-undecenyl-N-[(trichloromethyl)thio]succinimide; and
(6c) 2-dodecenyl-N-[(trichloromethyl)thio]succinimide ($n_D$ 1.5198).

The non-crystalline compounds of the invention are brownish, more or less viscous oils.

The compounds of the invention represented by the structural formula I where R is alkenyl having from 8 to 12 carbon atoms are active as fungicides and have good solubility in petroleum hydrocarbons. They are useful for application to and incorporation in materials to retard or prevent fungus growth which cause deterioration of such materials. For example they can be incorporated in oil-, alkyl resin-, Pergut- and other lacquers at higher concentrations (5% and greater) than known fungicides. They can also be employed to protect wood, leather, textiles, tent canvas, cardboard and paper against the deleterious effects of fungus. For such purpose, solutions in organic solvents as well as combinations with waxes, such as paraffin, are employed. They may also be employed as fungicidal agents to protect plants and in fruit cultivation.

The comounds of the invention can be prepared for use using conventional techniques. Thus they may be mixed with a suitable carrier, e.g., a solid carrier such as but not limited to clay, talc and bentonite; or with a suitable liquid carrier, e.g., as a solution in a solvent such as but not limited to petroleum hydrocarbons and alcohol, and as suspensions in a non-solvent. If desired, the compositions of the invention may, in order to broaden the spectrum of activity, have incorporated in them other suitable fungicidal compounds, e.g., fungicides belonging to the classes of 4-tert-butylphenylthioalkanols and 4-tert-butylphenoxyalkanols.

The amounts of the compounds or mixtures thereof to be applied in order to be fungicidally effective will vary depending on a number of factors, for example, on the nature of the material to be protected, and can readily be determined by one having ordinary skill in the art.

We claim:
1. A 2-R-N-[(trichloromethyl)thio]succinimide having the formula

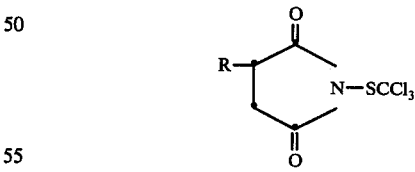

where R is alkenyl having from 8 to 12 carbon atoms.
2. A 2-R-N-[(trichloromethyl)thio]succinimide according to claim 1 wherein alkenyl is selected from the group consisting of octenyl, 2-isooctenyl, 2-nonenyl, 1-decenyl, undecenyl and dodecenyl.
3. A 2-R-N-[(trichloromethyl)thio]succinimide according to claim 2 wherein alkenyl is selected from the group consisting of 2-isooctenyl, 2-nonenyl and 1-decenyl.
4. A fungicidal composition comprising as active fungicidal ingredient at least one 2-R-N-[(trichloromethyl)thio]succinimide having the formula

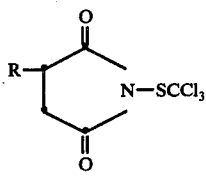

where R is alkenyl having from 8 to 12 carbon atoms, and a carrier therefor.

5. A fungicidal composition according to claim 4 wherein the active fungicidal ingredient is selected from at least one 2-R-N-[(trichloromethyl)thio]succinimide where R is selected from the group consisting of octenyl, 2-isooctenyl, 2-nonenyl, 1-decenyl, undecenyl and dodecenyl.

6. A fungicidal composition according to claim 5 wherein the active fungicidal ingredient is selected from at least one 2-R-N[(trichloromethyl)thio]succinimide where R is selected from the group consisting of 2-isooctenyl, 2-nonenyl and 1-decenyl.

7. A method for preventing or retarding the deleterious effects associated with fungus contamination on a material susceptible to fungus contamination which comprises treating the material with a fungicidally effective amount of at least one 2-R-N-[(trichloromethyl)thio]succinimide of the formula

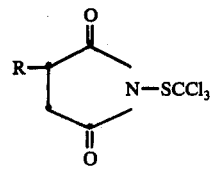

where R is alkenyl having from 8 to 12 carbon atoms.

8. A method according to claim 7 wherein the material is treated with at least one 2-R-N-[(trichloromethyl)thio]succinimide where R is selected from the group consisting of octenyl, 2-isooctenyl, 2-nonenyl, 1-decenyl, undecenyl and dodecenyl.

9. A method according to claim 7 wherein the material is treated with at least one 2-R-N-[(trichloromethyl)thio]succinimide where R is selected from the group consisting of 2-isooctenyl, 2-nonenyl and 1-decenyl.

* * * * *

UNITED STATES PATENT AND TRADEMARK OFFICE
CERTIFICATE OF CORRECTION

PATENT NO. : 4,085,220

DATED : April 18, 1978

INVENTOR(S) : Wilhelm Sandermann, Heinz Eggensperger and Karl-Heinz Diehl

It is certified that error appears in the above–identified patent and that said Letters Patent are hereby corrected as shown below:

Column 2, line 30, "Capstan" should read -- Captan --.

Column 2, line 66, "notes" should read -- noted --.

Column 5, Table 2, "0.2" should read -- 0.1 --.

Signed and Sealed this

Twenty-third Day of January 1979

[SEAL]

Attest:

RUTH C. MASON
Attesting Officer

DONALD W. BANNER
Commissioner of Patents and Trademarks